United States Patent
Scheuerer et al.

(10) Patent No.: US 12,127,840 B2
(45) Date of Patent: Oct. 29, 2024

(54) SYSTEM AND METHOD FOR PREPARING, VISUALIZING AND ANALYZING A DIGITAL IMAGE FOR COMPUTERIZED PSYCHOTHERAPY

(71) Applicants: Joachim Scheuerer, Tiefencastel (CH); Peter Brugger, Valens (CH)

(72) Inventors: Joachim Scheuerer, Tiefencastel (CH); Peter Brugger, Valens (CH)

( * ) Notice: Subject to any disclaimer, the term of this patent is extended or adjusted under 35 U.S.C. 154(b) by 418 days.

(21) Appl. No.: 17/691,138

(22) Filed: Mar. 10, 2022

(65) Prior Publication Data
US 2023/0284947 A1    Sep. 14, 2023

(51) Int. Cl.
*A61B 5/16* (2006.01)
*G06F 3/01* (2006.01)
*G06T 3/60* (2006.01)

(52) U.S. Cl.
CPC .............. *A61B 5/165* (2013.01); *A61B 5/167* (2013.01); *G06F 3/011* (2013.01); *G06T 3/60* (2013.01); *G06T 2203/011* (2013.01)

(58) Field of Classification Search
CPC ......... A61B 5/165; A61B 5/167; G06F 3/011; G06F 2203/011; G06T 3/60; G06T 2200/24; G06T 11/60
See application file for complete search history.

(56) References Cited

U.S. PATENT DOCUMENTS

| | | |
|---|---|---|
| 8,235,725 B1 | 8/2012 | Hill |
| 9,833,184 B2 | 12/2017 | Derchak et al. |
| 11,048,921 B2 | 6/2021 | Sorci et al. |
| 2015/0305662 A1 | 10/2015 | Kilmer et al. |

FOREIGN PATENT DOCUMENTS

WO   WO 2020/074878   4/2020

OTHER PUBLICATIONS

Almeida, A. (2017). Digital diagnosis of protruding ears.
Anda, F., Lillis, D., Le-Khac, N. A., & Scanlon, M. (May 2018). Evaluating automated facial age estimation techniques for digital forensics. In 2018 IEEE Security and Privacy Workshops (SPW) (pp. 129-139). IEEE.
Blekić, W., Arachchige, K. K., Wauthia, E., Loureiro, I. S., Lefebvre, L., & Rossignol, M. (2021). Affective ratings of pictures related to interpersonal situations. Frontiers in psychology, 12.
(Continued)

*Primary Examiner* — Huo Long Chen
(74) *Attorney, Agent, or Firm* — Walter J. Tencza, Jr.

(57) ABSTRACT

A computerized method for performing psychoanalysis on a human being, the method performed on a computing device having a display screen operating a graphical user interface, the method including the steps of providing an image to the computing device, the image representing human, animal, human-like, or animal-like facial features, generating a mirrored image from the provided image about a vertical mirror axis with a data processor of the computing device, partially superposing the provided image and the mirrored image to create a vertical axi-symmetric image, one side of the vertical mirror axis showing a portion of the provided image, the other side showing a portion of the mirrored image, and displaying the vertical axi-symmetric image on the graphical user interface of the computing device.

19 Claims, 14 Drawing Sheets

(56) References Cited

OTHER PUBLICATIONS

Borod, J. C., Haywood, C. S., & Koff, E. (1997). Neuropsychological aspects of facial asymmetry during emotional expression: A review of the normal adult literature. Neuropsychology review, 7(1), 41-60.
Chi, N. C., & Demiris, G. (2015). A systematic review of telehealth tools and interventions to support family caregivers. Journal of telemedicine and telecare, 21(1), 37-44.
Chotard, H., Ioannou, S., & Davila-Ross, M. (2018). Infrared thermal imaging: Positive and negative emotions modify the skin temperatures of monkey and ape faces. American journal of primatology, 80(5), e22863.
Crowley, K., Sliney, A., Pitt, I., & Murphy, D. (Jul. 2010). Evaluating a brain-computer interface to categorise human emotional response. In 2010 10th IEEE International Conference on Advanced Learning Technologies (pp. 276-278). IEEE.
Cruz-Albarran, I. A., Benitez-Rangel, J. P., Osornio-Rios, R. A., & Morales-Hernandez, L. A. (2017). Human emotions detection based on a smart-thermal system of thermographic images. Infrared Physics & Technology, 81, 250-261.
Cunningham, N. R., Ely, S. L., Garcia, B. N. B., & Bowden, J. (2021). Addressing pediatric mental health using telehealth during COVID-19 and beyond: A narrative review. Academic Pediatrics.
Heesacker, M., Perez, C., Quinn, M. S., & Benton, S. (2020). Computer-assisted psychological assessment and psychotherapy for collegians. Journal of clinical psychology, 76(6), 952-972.
Jin, B., Qu, Y., Zhang, L., & Gao, Z. (2020). Diagnosing Parkinson disease through facial expression recognition: video analysis. Journal of Medical Internet Research, 22(7), e18697.
Koff, E., Borod, J. C., & White, B. (1981). Asymmetries for hemiface size and mobility. Neuropsychologia, 19(6), 825-830.
Kohut, H. (2013). The analysis of the self: A systematic approach to the psychoanalytic treatment of narcissistic personality disorders. University of Chicago Press. ABSTRACT & Link in google books: https://books.google.nl/books?hl=fr&lr=&id=VP_HKrnz-DUC&oi=fnd&pg=PR1&dq=% E2%80%9CThe+An.
Lang, P. J. (1979). A bio-informational theory of emotional imagery. Psychophysiology, 16(6), 495-512.
Lang. P. J. (2005). International affective picture system (IAPS): Affective ratings of pictures and instruction manual. Technical report.
Lang, P. J., Bradley, M. M., & Cuthbert, B. N. (1997). International affective picture system (IAPS): Technical manual and affective ratings. NIMH Center for the Study of Emotion and Attention, 1(39-58), 3.
Lopes-Santos, J. A., Martins, C., La Fuente, J. M., & Costa-Carvalho, M. F. (2017). A novel approach for classifying protruding ears is easy to calculate and implement in daily clinical practice. Acta Paediatrica, 106(9), 1525-1530.
Nicholls, M. E., Ellis, B. E., Clement, J. G., & Yoshino, M. (2004). Detecting hemifacial asymmetries in emotional expression with three-dimensional computerized image analysis. Proceedings of the Royal Society of London. Series B: Biological Sciences, 271(1540), 663-668.
Nummenmaa, L., Glerean, E., Hari, R., & Hietanen, J. K. (2013). Bodily maps of emotions. Proceedings of the National Academy of Sciences, 111(2), 646-651.
Othmani, A., Taleb, A. R., Abdelkawy, H., & Hadid, A. (2020). Age estimation from faces using deep learning: A comparative analysis. Computer Vision and Image Understanding, 196, 102961.
Salazar-López, E., Domínguez, E., Ramos, V. J., De la Fuente, J., Meins, A., Iborra, O., . . . & Gómez-Milán, E. (2015). The mental and subjective skin: Emotion, empathy, feelings and thermography. Consciousness and cognition, 34, 149-162.
Smith, W. M. (2000). Hemispheric and facial asymmetry: gender differences. Laterality: Asymmetries of Body, Brain and Cognition, 5(3), 251-258.
Tamagni, C., Mantei, T., & Brugger, P. (2009). Emotion and space: Lateralized emotional word detection depends on line bisection bias. Neuroscience, 162(4), 1101-1105.
Thompson, J. K. (1985). Right brain, left brain; left face, right face: Hemisphericity and the expression of facial emotion. Cortex, 21(2), 281-299.
Wang, Y., & Yuan, B. (2001). A novel approach for human face detection from color images under complex background. Pattern Recognition, 34(10), 1983-1992.
Yow, K. C., & Cipolla, R. (1997). Feature-based human face detection. Image and vision computing, 15(9), 713-735.

SYSTEM AND METHOD FOR PREPARING, VISUALIZING AND ANALYZING A DIGITAL IMAGE FOR COMPUTERIZED PSYCHOTHERAPY

FIELD OF THE INVENTION

The present invention is directed to the field of computer systems and methods for using digital images for psychotherapy, more precisely in the field of eliciting emotions by the use of modified or manipulated images, and systems and methods of analyzing these emotions via a computer system.

BACKGROUND

Pictures and film clips are widely used and accepted stimuli to elicit emotions for psychological research and for psychoanalysis in human beings. See for example Peter J. Lang, "A Bio-Informational Theory of Emotional Imagery," Psychophysiology, Vol. 16, pp. 495-512, year 1979. The use of pictures has been a common method for the induction of emotional states in a human being, and it can be easily standardized, as exemplified by The International Affective Picture System (TAPS), which provides a validated set of standardized photographs now used internationally for a broad range of research applications. See Lang et al., "International Affective Picture System (TAPS): Technical Manual and Affective ratings." NIMH Center for the Study of Emotion and Attention, Vol. 1, year 1997, pp. 39-58. Emotional effects to human being induced by presentation of the stimuli were quantified using a paper-and-pencil version of the Self-Assessment Manikin scale (SAM). Results of the affective processing have shown to be a valuable way to get a profound insight into non-conscious affective processing of such images by a human being.

Moreover, manual assessments methods have been proposed, based on the paper-and-pencil version of the Self-Assessment Manikin scale (SAM). See Peter J. Lang, "International affective picture system (TAPS): Affective ratings of pictures and instruction manual," Technical Report, year 2005. This manual assessment method is based on valence and arousal, illustrated by little manikins depicting five steps from unhappy to happy (valence) and from calm to excited (arousal), respectively. In the field of analyzing human emotions related to interpersonal situations, a new set of standardized stimuli containing images depicting interpersonal situations, both positive and negative, have been used, that allows to make a sensitive assessment of a wide range of cognitions linked to social interaction. including but not limited to empathy, perspective taking, traumatic experiences. See Blekić et al., "Affective Ratings of Pictures Related to Interpersonal Situations," Frontiers in psychology, Vol. 12, year 2021.

However, most methods for psychiatric and psychotherapeutic analysis of human being rely on standard images, for example photos or videos that show natural scenes, people or animals, and little exploration has been done with the use of manipulated images, and the specific emotions that can be caused to humans, and the analysis of these emotions. Therefore, substantially improved methods are desired, with the goal to extract additional and more complex information from a subject, for example for psychiatric and psychotherapeutic analysis.

SUMMARY

According to one aspect of the present invention, a system for performing psychoanalysis on a human being is provided, the system including a computing device including a display screen operating a graphical user interface and a data processor. Preferably, the data processor of the computer system is configured to access an image, the image representing human, animal, human-like, or animal-like facial features, generate a mirrored image from the provided image about a vertical mirror axis with a data processor of the computing device, partially superpose the provided image and the mirrored image to create a vertical axi-symmetric image, one side of the vertical mirror axis showing a portion of the provided image, the other side showing a portion of the mirrored image, and display the vertical axi-symmetric image on the graphical user interface of the computing device.

According to another aspect of the present invention, a computerized method for performing psychoanalysis on a human being is provided, the method performed on a computing device having a display screen operating a graphical user interface, for example a personal or Macintosh computer. Preferably, the method includes the steps of providing an image to the computing device, the image representing human, animal, human-like, or animal-like facial features, generating a mirrored image from the provided image about a vertical mirror axis with a data processor of the computing device, partially superposing the provided image and the mirrored image to create a vertical axi-symmetric image, one side of the vertical mirror axis showing a portion of the provided image, the other side showing a portion of the mirrored image, and displaying the vertical axi-symmetric image on the graphical user interface of the computing device.

According to still another aspect of the present invention, a non-transitory computer readable medium having computer instructions recorded thereon is provided, the computer instructions configured to perform a method when executed on a computer system having a display device. Preferably, the method is configured to perform psychoanalysis on a human being, the method including the steps of providing an image to the computing device, the image representing human, animal, human-like, or animal-like facial features, generating a mirrored image from the provided image about a vertical mirror axis with a data processor of the computing device, partially superposing the provided image and the mirrored image to create a vertical axi-symmetric image, one side of the vertical mirror axis showing a portion of the provided image, the other side showing a portion of the mirrored image, and displaying the vertical axi-symmetric image on the graphical user interface of the computing device.

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF THE SEVERAL DRAWINGS

The accompanying drawings, which are incorporated herein and constitute part of this specification, illustrate the presently preferred embodiments of the invention, and together with the general description given above and the detailed description given below, serve to explain features of the invention.

FIG. 1 shows a perspective, exemplary view of a computer system 100 that can be used to perform the method according to an aspect of the present invention, including a data processing device 30, a display screen 10, different types of data input devices such as a keyboard 20, a trackpad 26, a mouse 22, a touch screen interface 24, network 50, and remote or local database 60, and with a graphical user interface 40 shown on display screen 10;

Figure 5:
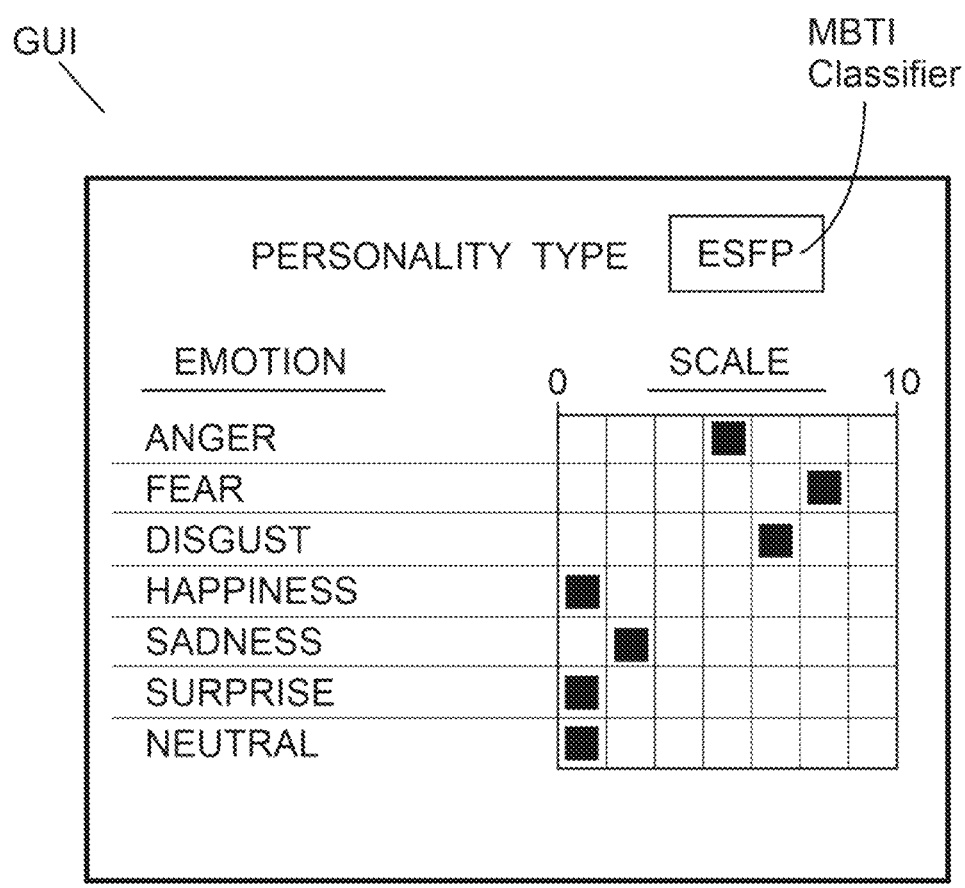
Figure 6A:
Figure 6B:
Figure 6C:

FIG. 5 shows an exemplary and simplified result screen providing for results of the evaluation or analysis performed in step S90; and FIGS. 6A to 6G show a series of photo examples of the application of the method to a photo of the musician David Bowie, showing an original digital photograph of the face in FIG. 6A, showing a two right sides with RS, RSM in FIG. 6B, showing two left sides with LS, LSM in FIG. 6C, showing a superposition of transparent semi-faces in FIGS. 6D, 6E, 6F, and 6G, with mirrored face halves that are merged by superposed transparent images LST, LSMT.

Herein, identical reference numerals are used, where possible, to designate identical elements that are common to the figures. Also, the representations in the figure are simplified for illustration purposes and may not be depicted to scale.

DETAILED DESCRIPTION OF THE SEVERAL EMBODIMENTS

Figure 1:
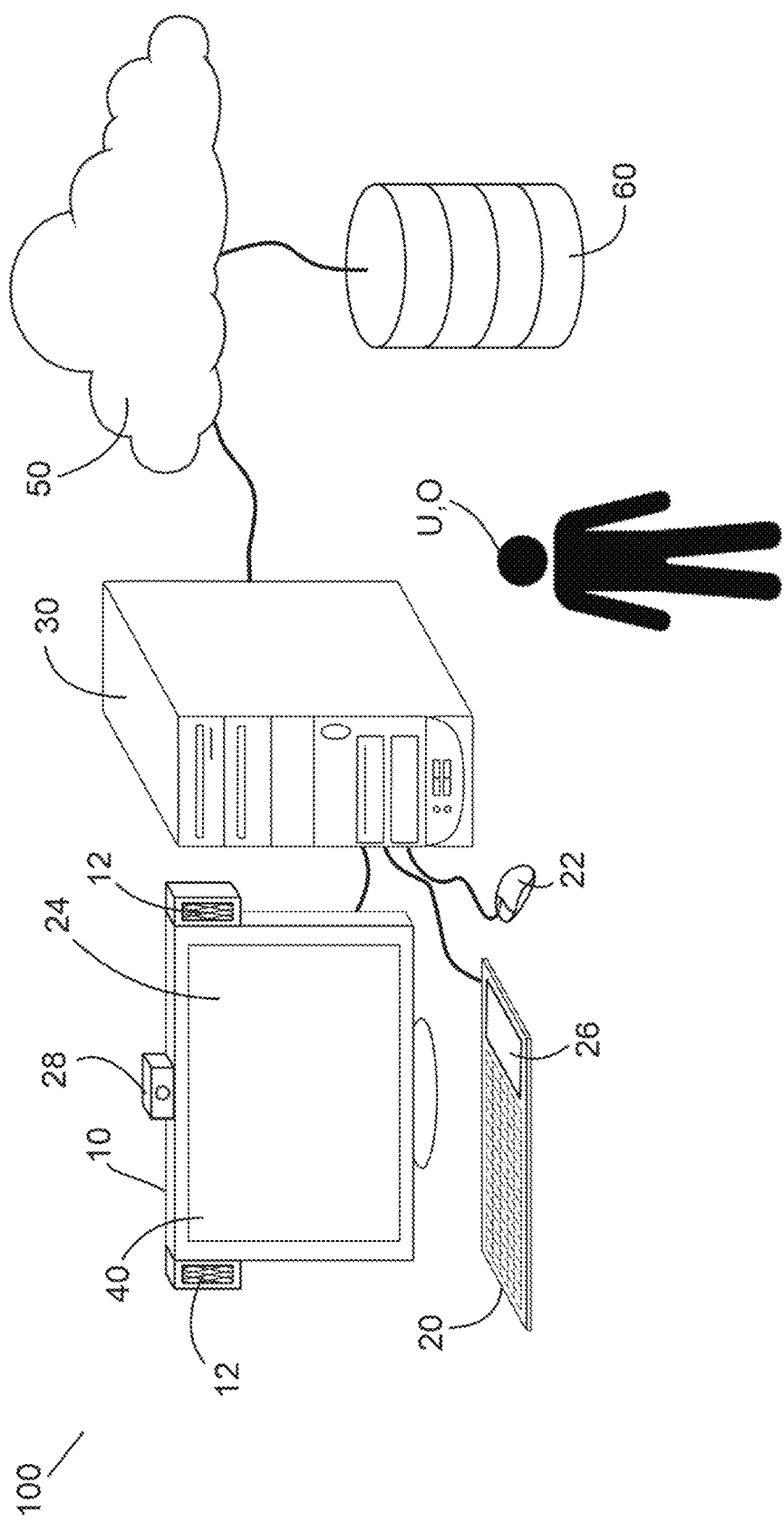

FIG. 1 shows a perspective, exemplary view of a computer system 100 that can be used to perform one or more steps of method M100 according to an aspect of the present invention, the system 100 including a data processing device 30, for example a desktop computer unit or other type of data processing device, a display screen 10 as a data output or presentation device having speakers 12, different types of data input devices that allow a user U or living being to enter data in different ways, such as a keyboard 20, a trackpad 26, a mouse 22, a camera 28, a touch screen interface 24, these devices operatively interconnected to data processing device 30. Moreover, data processing device 30 can also be connected to a network 50, for example the internet, an intranet, or other types of local or global networks, for example to access clouds or databases 60. Data processing device 30 can be configured to read and execute computer readable instruction code that can perform the method M100, for example when executed by one or more data processors, for example and can generate a graphical user interface (GUI) 40 that is provided on display screen 10, of providing a user interface. Computer system 100 can also be but is not limited to a smart phone, a tablet, a notebook computer, a laptop computer, a personal computer (PC), a Macintosh computer, or other types of data processing devices.

Figure 2:
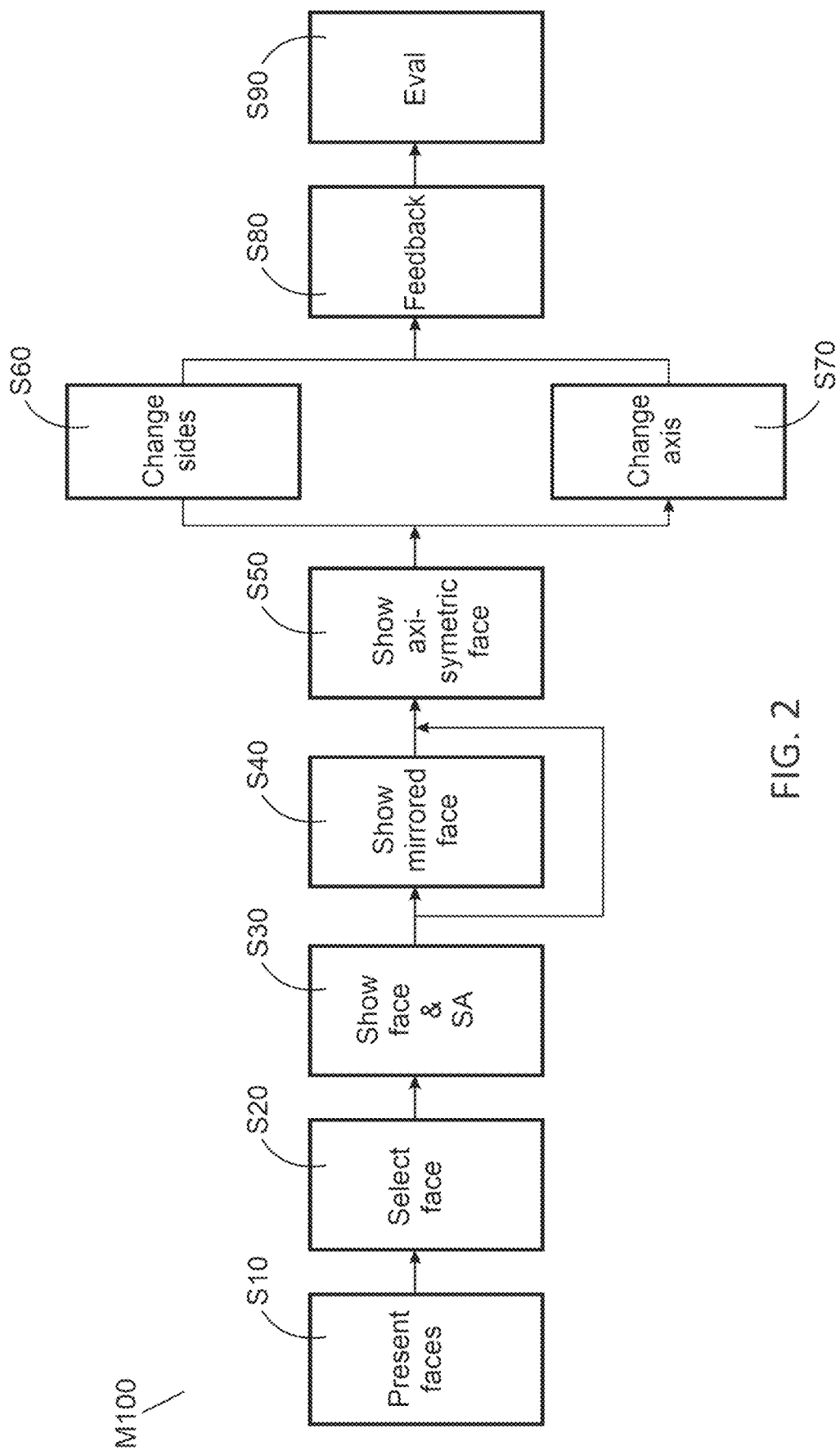
FIG. 2 shows a flowchart with different steps of a method M100 for performing the psychoanalysis with a computer system, for example the one shown in FIG. 1, according to another aspect of the present invention.

FIG. 2 shows an exemplary flowchart of the method M100 for selecting, preparing and visualizing a digital image for psychotherapy and other types of uses, for example by the use of computer system 100 shown in FIG. 1, preferably using a graphical user interface 40 to present the images to the user U, and to allow user for user interaction. In a first step S10, for example after launching an application software on a computing device 30, a graphical user interface GUI 40 can be presented on display screen 10, where different images FI1 to FI4 can be presented, these images FI1 to FI4 providing for a front-view portrait of a human, human-like or other living being, for example images that represent faces of different human beings. In the variant shown, four (4) different images FI1 to FI4 are shown on the same screen of GUI 40, but there can be more or less than four (4) of such images, and they can be scrollable or displayed one-by-one. It is also possible that images FI1 to FI4 are presented having different types of faces or facial features, for example a plurality of images representing human faces and facial features, animal faces and facial features, human-like faces and facial features, metaphorical representations of a human face, or animal-like faces and facial features, or are presenting facial features with or without other body features of a statue, a painting, a photograph, or other types of representation of a face or facial features. It is also possible that the images are self-portraits of the user U, for example different self-portraits of a face of user U with different moods that have previously been taken and have been provided for access by computing device 30. These different images FI1 to FI4 with faces, facial features, or facial-like features can be presented to user U such that the user can select one of these images, for example by moving a selector SE as a graphical element relative to the images FI1 to FI4, for example a box, an arrow, and indicator, a shading, a highlighting, or other type of graphical indication of a selection. In the example shown, graphically represented arrows AR or other types of graphical interface elements can be displayed to move the selector SE, and user can press, touch, or otherwise select arrows AR to move to the next representation for selection.

In a variant, it is possible that user U or operator O already knows which facial image of a human being or human-like being he or she wants to use for method M100, and therefore there is no need to choose from images FI1 to FI4, or other images. For example, a psychologist may instruct user U to bring a photo of an individual with him or with her, or to send or upload such photo, the individual known to user U to evoke positive emotions or negative emotions, or some other specific mood or feeling related to the individual having his or her face represented on the photo. This photo can thereby be scanned by a scanner and provided as a digital image to system 100, digitally captured by camera 28, or otherwise made available to system 100, for example by sending a digital image of a face of an individual per email that can be accessed by system 100, or by uploading a specific image of a face of an individual to a server for use in method M100, to provide for a selected image CS, or to use a browsing feature to select an image from a folder system of a cloud storage space.

Next, with a step S20 user U can select one of the images FI1 to FI4 for further processing with method M100 by the use of the graphical user interface 40, for example but not limited to a selection with the return key of keyboard 20, double-click with mouse 22 or trackpad 26 by using a cursor or arrow, or by activating, touching or pressing a dedicated button of the GUI 40. For example, the user U can select one image FI by moving selector SE over an image FI for having a face or facial features that evoke specific emotions in him or her, for example positive, negative, or neutral feelings, for example but not limited to feelings of nostalgia, fear, happiness, pride, trust, distrust, disgust, romance. In this respect, user U who selects image FI to designate a selected image CS preferably is a human being or patient of a psychoanalyst, psychotherapist, or psychologist, or a human being or patient that would like to participate in a self-psychoanalysis. Preferably, user U selects the image FI as a stimulus for his own analysis, whether by himself, herself, or assisted by a professional, but his choice should be based on the feelings or emotions that he associates with the face or face-like representation of image FI.

Next, a step S30 can be performed, where the selected image CS that is based on image SD is shown in a window or other part of graphical user interface 40, so that the user U can perform specific modifications to selected image CS. For example, a symmetrical axis line SA can be displayed, arranged to be substantially vertically relative to selected image CS, and for example initially arranged along a center line of image CS or centered relative to the displayed face or facial-like representation. Symmetrical axis line SA can define an axis where the selected image CS will be mirrored into two axi-symmetrical parts, to form a new axi-symmetric mirrored image NI, as further explained below. Symmetrical axis SI can be displayed as a semi-transparent or translucid line, as a dotted, dashed line, or solid line, or combination thereof, or other types of graphical visualizations. This axis SA is indicative of a mirror line that will be applied to the selected image CS, to thereby generate a new axi-symmetric mirrored image NI that is composed of either two left sides LS of selected image CS, or of two right sides RS of selected image CS, the mirror axis being defined by the placement of line SA in a horizontal direction. For example, initially, symmetrical axis line SA1 can be displayed in the geometric middle of face that is represented by selected image CS, for example by an image processing algorithm that can determine a center of a head, for example by using the center of the eye sockets and nostrils, or by centroid detection after clipping. See for example Wang et al., "A Novel Approach for Human Face Detection from Color Images under Complex Background," Pattern Recognition 34, No. 10, year 2001, pp. 1983-1992.

As another example for step S30, it is possible to perform image processing of selected image CS to detect a middle point of the interpupillary distance of the face or face-like presentation of the frontal view, for example by first detecting a coordinate position of the left and the right pupils of the face or face-like representation of selected image CS, and then calculating a coordinate position of the middle point of the two positions. Thereafter, the symmetrical axis line SA can be placed to cross the coordinate position of the middle point that was determined, to be a vertical with respect to the displayed selected image CS. See for example Smith, William M., "Hemispheric and Facial Asymmetry: Gender Differences," Laterality: Asymmetries of Body, Brain and Cognition, Vol. 5, No. 3, year 2000, pp. 251-258. It is also possible that step S30 compensates for a misorientation of the face or face-like representation of selected image CS, for example in a case where the face is not arranged vertically, for example by an off-angle quasi vertical orientation, by a certain angle. In such case, the computer algorithm can perform a step of face detection and orientation estimation, and can either provide for a new selected image CS with a re-oriented face or face-like representation, to have a vertical alignment that is compensated by the off-angle. Also, in a variant, it is possible to provide for a symmetrical axis line SA that is not displayed perfectly vertically to the selected image CS, but to be parallel to a vertical extension of the face or face-like representation of selected image CS, to match with the off-angle vertical position of the face. See for example Yow et al., "Feature-Based Human Face Detection," Image and Vision Computing, Vol. 15, No. 9, year 1997, pp. 713-735. Thereby, symmetrical axis line SA can be displayed rotated by the off-angle on GUI 40.

Figure 3A:
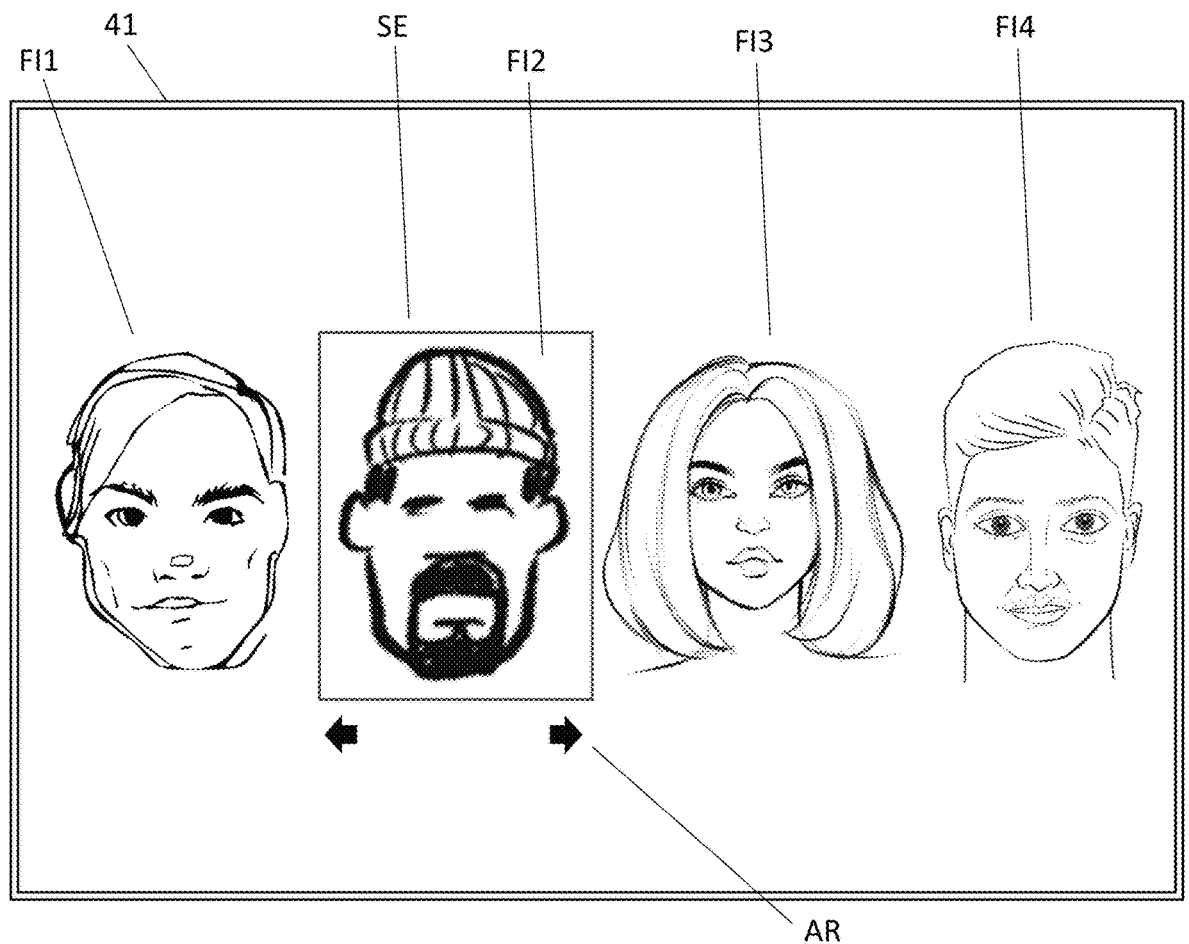
FIGS. 3A to 3H show an exemplary representation of a line drawing of a face of a male human, illustrating the results of the different image data processing steps.
Figure 3B:
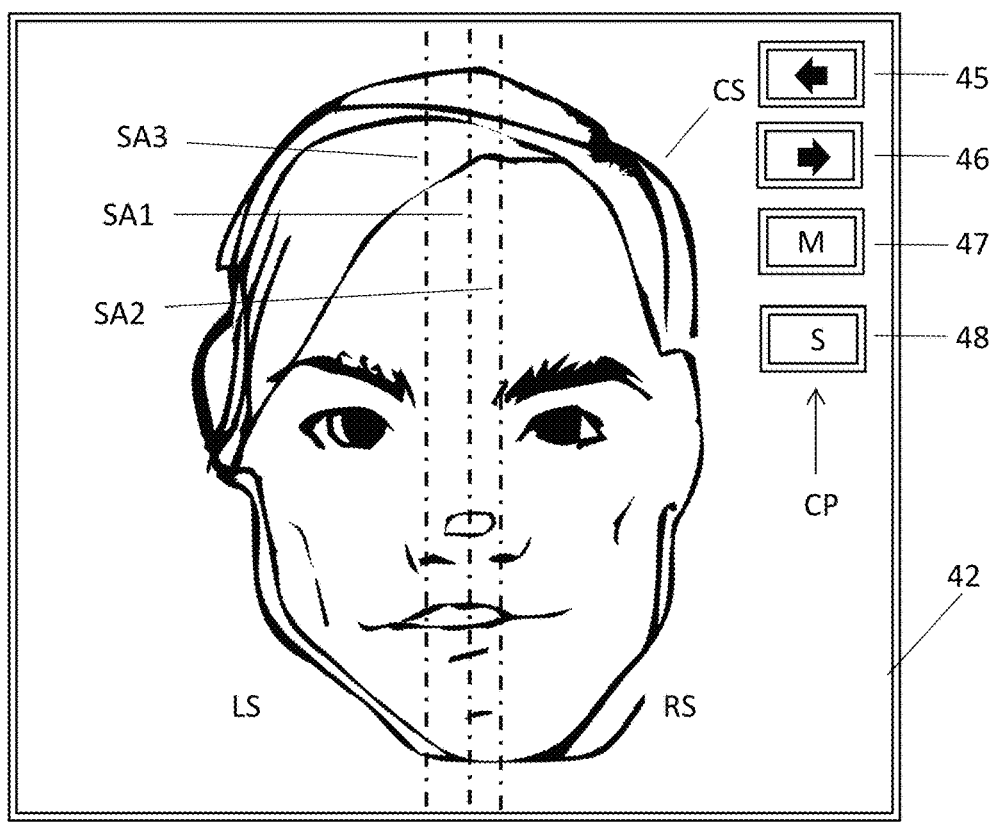

User U can now move to change a position of the vertical mirror axis defined by center line SA that will be applied to the face or facial-like image of the selected image CS, to thereafter create an axi-symmetric image of the face of selected image CS, by moving symmetrical axis line SA more to the left as visualized with line SA3, or move it more to the right as visualized with line SA2, for example by using buttons 45, 46, or by directly selecting and moving symmetrical axis line SA with a cursor, or by clicking on the line and dragging it to the left or to the right. This allows user U to visualize at which location the selected image CS will be mirrored or flipped to allow the computerized formation of two axi-symmetrical parts. It is thereby possible to move center line SA by the user or operator far away from the initial middle position, for example to move it close to or even beyond the displayed face. Thereafter, by activating, pressing, or otherwise selecting button 48 labelled with "S", or entering an equivalent command to the computer system 100, user U can generate the axi-symmetric mirrored image NI based on the current position of the symmetrical axis line SA, with different examples shown in FIGS. 3D to 3H. In this respect, a chosen one of symmetrical axis line SA, for example SA1, SA2, or SA3 as shown in FIG. 3B, for example SA1 that leads through the midpoint of the horizontal line connecting the pupils of the eyes, is displayed on the GUI, and each of the two halves of the face or face-like representation is flipped and merged with its ipsilateral half to form a right-right composite face and a left-left composite face, to show an axi-symmetric image NI of the composite face.

Figure 3C:
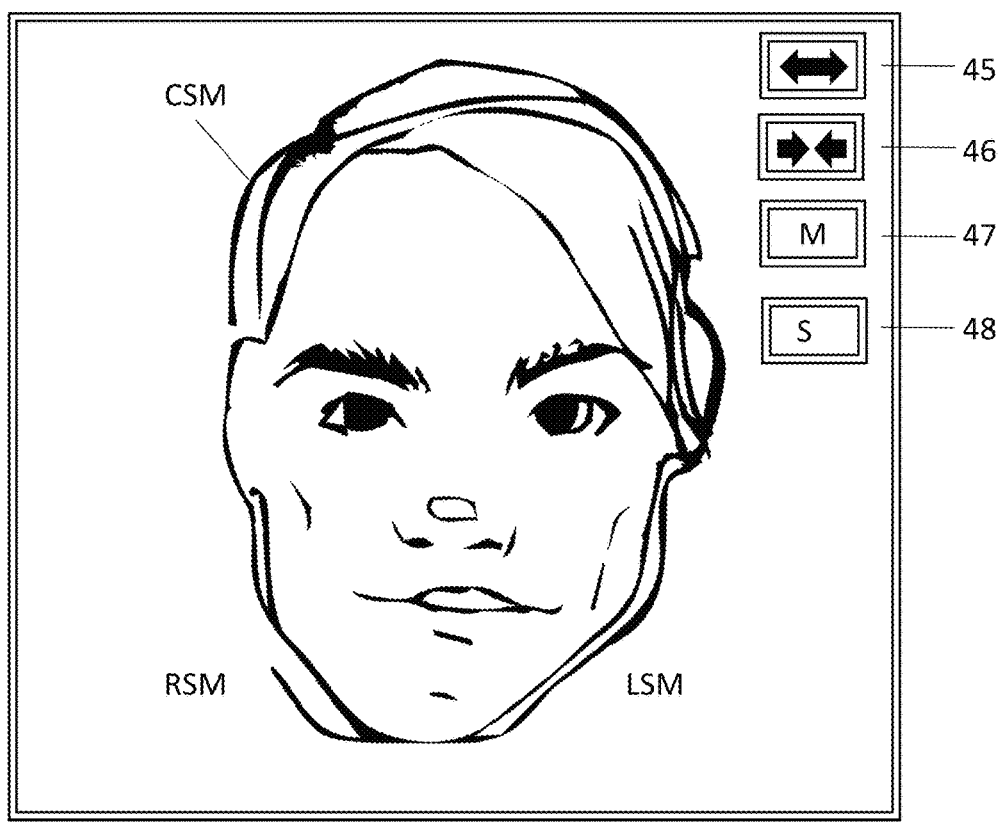

Moreover, method M100 can optionally include a step S40, in which by activating, pressing, or otherwise selecting button 47 labelled with "M", or entering an equivalent command to the computer system 100, it is possible to display a mirror image CSM of selected image CS, as shown in FIG. 3C, so that user U can also evaluate mirror image CSM on his feelings that are caused or evoked by mirror image CSM.

Figure 3D:
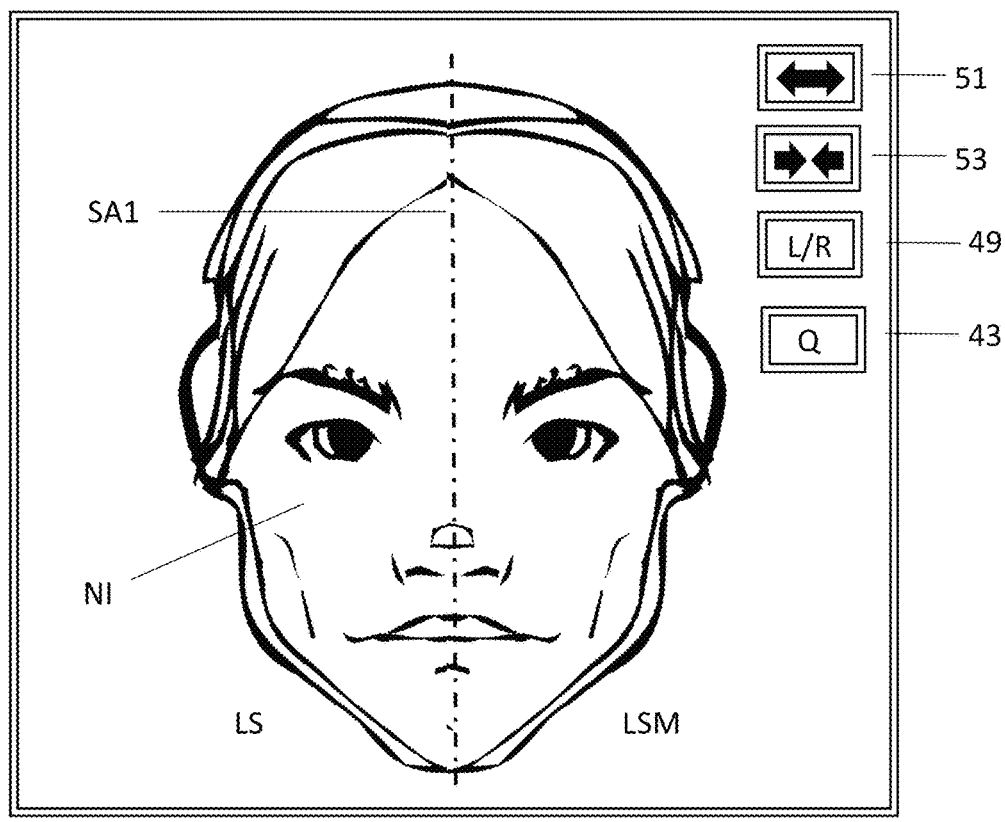
Figure 6D:
Figure 6E:
Figure 6F:
Figure 6G:

For example, with FIG. 3D, with step S50 of method 100, an axi-symmetric image NI can be generated and shown after user U has pressed or otherwise activated button 48, where the selected image CS, and a mirror image of the selected image CS, like the one shown in FIG. 3C, have been merged to show a the axi-symmetric image NI, composed of a non-mirrored left side LS of the face of selected image CS and a mirrored left side LSM of mirrored image CSM. In this respect, an image of a composite face is produced and displayed with NI, also referred to as a L/R composite face. In a variant, this image can be done by using a semi- or otherwise partially transparent, fully-transparent, or translucid superposition of left side LS and mirrored left side LSM, as shown in the examples of FIGS. 6D, 6E, 6F, and 6G for example referred to as the transparent left side LST and the transparent mirrored left side LSMT, or the transparent right side RST or the transparent mirrored right side RSMT. This can be done by different image processing algorithms, for example by creating a mirrored image CSM of CS, cutting of the right-side portions of both images CSM and CS at the chosen symmetrical axis line SA, and then merging the two halves together, to show an axi-symmetric face or face-like representation with image NI of a composite face in the graphical user interface GUI, the result thereof shown in FIG. 3D. Different transparency or translucidity settings can be applied to the half-faces, for merging the different sides of the images CS, CSM. As a variant, it is possible to superpose the selected image CS and mirrored image CSM to cover the right side RS of selected image CS. Regardless of the image processing method chosen, the result is a partially superposed image that has two sides that are identical but for the mirrored view thereof, composed of either two left sides LS or two right sides RS, for example as shown in an example in FIGS. 6B and 6C. In a variant, this image can be done by using a semi- or otherwise partially transparent, fully-transparent, or translucid superposition of left side LS and mirrored left side LSM, as shown in the examples of FIGS. 6D and 6E.

Figure 3E:
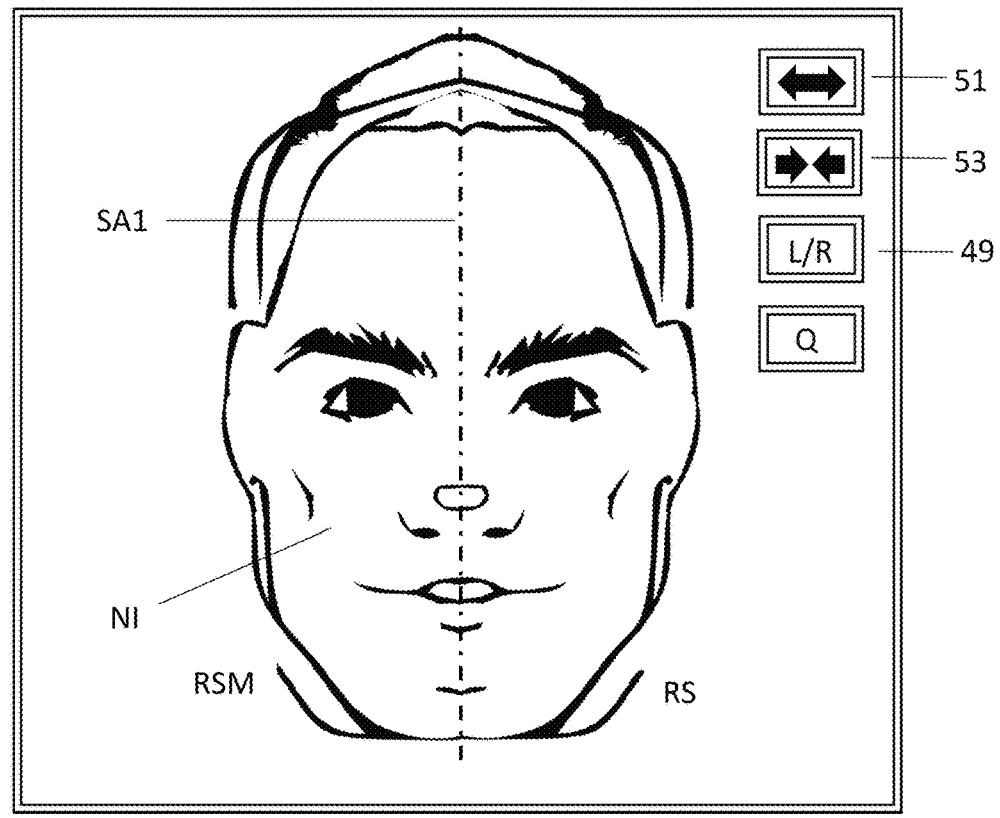
Figure 3F:
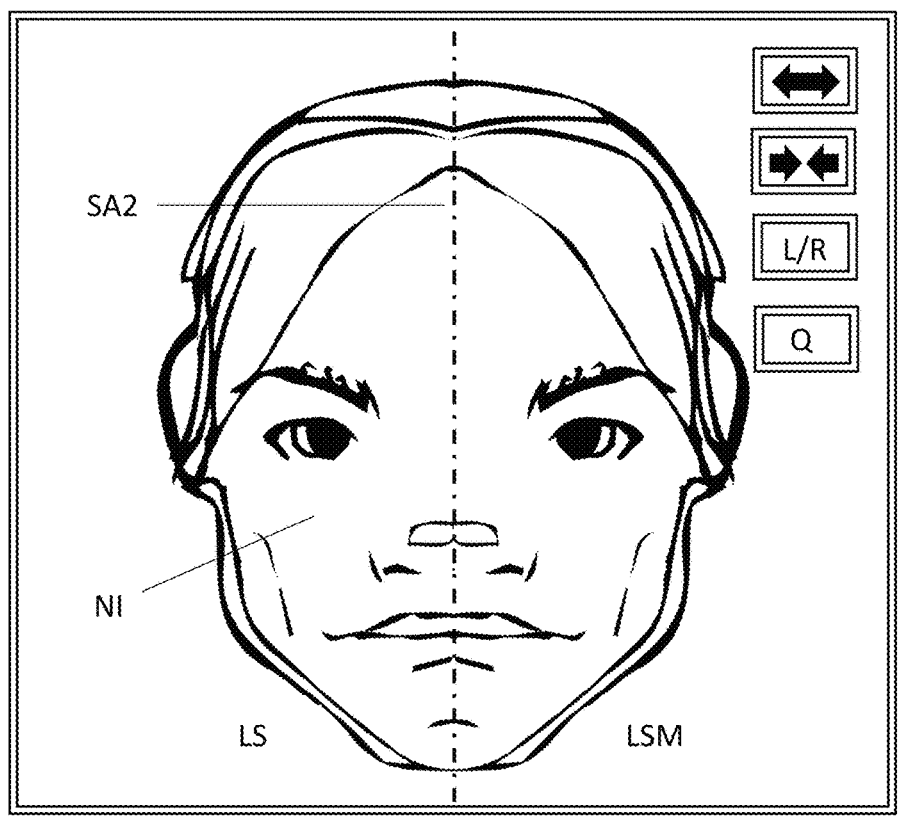
Figure 3G:
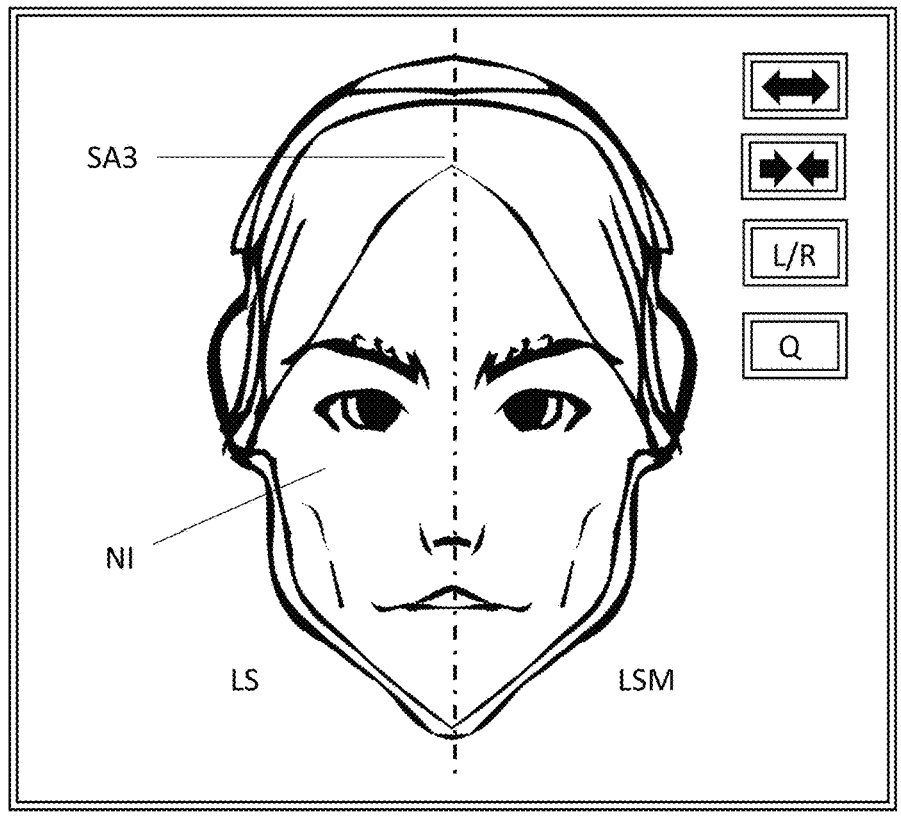
Figure 3H:
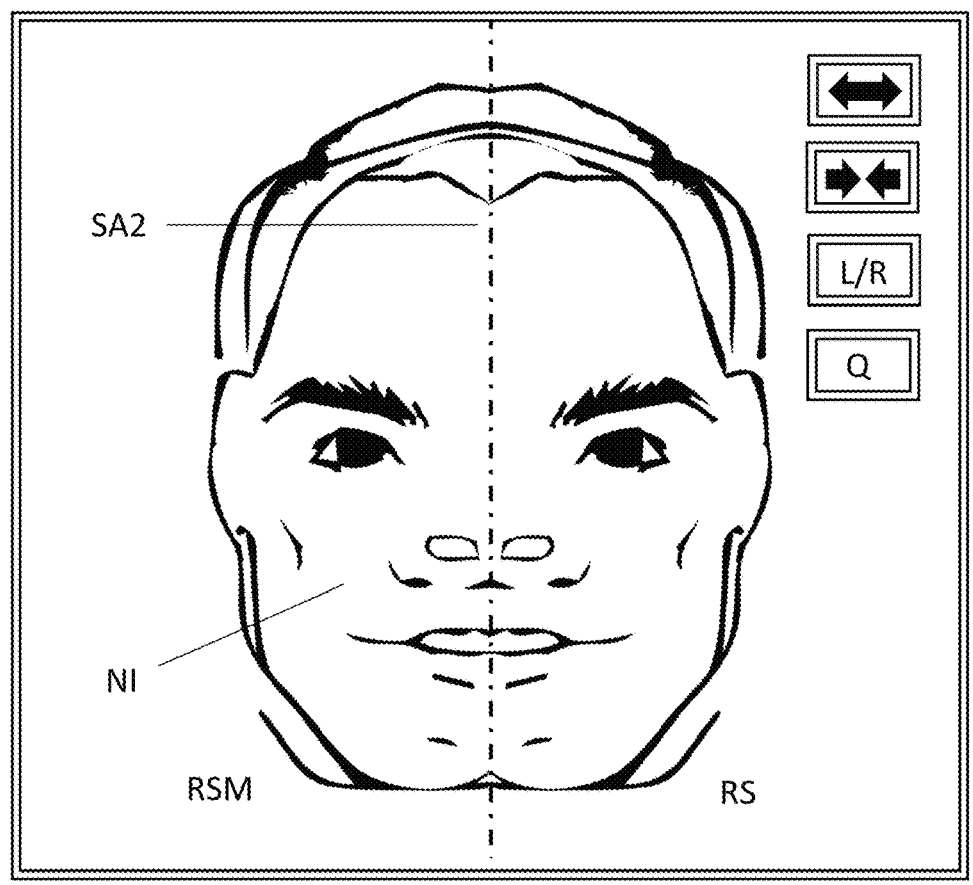

With elements 51, 53, and 49, user U can now modify the axi-symmetric image NI of the composite face, to create different types of views thereof, specifically different types of axi-symmetric views. For example, with a step S60, as shown in FIG. 3E with an exemplary window of the graphical user interface 40, user U can maintain symmetrical axis line SA1 at the same central location, but switch out the displaying of the left side LS and the mirrored left side LSM, but use the right side RS and the mirrored right side RSM, thereby changing the sides of the image NI of the composite face. This can be done by activating, pressing, or otherwise selecting button 49 labelled with "L/R", or entering an equivalent command to the computer system 100, to switch to left side view or right side view. This allows to generate a view of the same chosen face or face-like image CS to generate a different image composition. As can be seen between FIGS. 3D and 3E, and entirely different facial expression and facial demeanor may appear, depending on the overall symmetry of the face or face-like representation of the chosen image CS. User U can thereafter look at, study, or meditate to the newly appeared face as shown in FIG. 3E.

With a step S70, a horizontal position of the symmetrical axis line SA can be changed by user U, to generated different types of symmetric images of a face or face-like representation, as shown in the exemplary windows of the graphical user interface 40 of FIGS. F, G, and H. For example, by pressing, activating, or otherwise selecting an arrow button 51, the image NI of the composite face showing an axi-symmetric face or face-like representation of selected image CS can be expanded, for example changing the view of FIG. 3D to the view of FIG. 3F, for example thereby moving the application of symmetrical axis line SA from position SA1 to position SA2, or different intermediate positions thereof, for the image composed of left side LS and mirrored left side image LSM. This changes the appearance of the face or face-like representation, as showing a wide face with some widened facial feature, in particular the nose, mouth, chin, as they are arranged at the center axis of the face or face-like representation. With arrow button 53 or other equivalent command, the view of the image NI of the composite face having a face or face-like representation can be narrowed again, for example by moving the application of symmetrical axis line SA from position SA2 back to position SA1, or different intermediate positions thereof. Also, with step S70, by the use of arrow button 53 or other equivalent command, the view of the image NI of the composite face having a face or face-like representation can be further narrowed, or narrowed from the view of FIG. 3D, thereby moving the application of symmetrical axis line SA from position SA1 to position SA3, or an intermediate position thereof, to show a narrowed face, as exemplarily illustrated in FIG. 3G. With step S70, user U can freely choose a width of the image NI of the composite face having a face or face-like representation, by widening or narrowing an initial representation thereof. This is of course also possible with the axi-symmetric image of the right side RS and the mirrored right side RSM, as shown exemplarily in FIG. 3G.

It also possible that user U preforms different types of image transformations with an optional step S75, other types of image manipulations, filters, and transformations, for example by using different image processing algorithms that can be activated by an icon or other user input device of button menu or control panel CP of graphical user interface GUI, for example but not limited to darken the image, lighten the image, to change colorizations, to provide for pixilations, cartoonization, or abstraction of image IN, to add for a background image. Also, while in the context of this description and figures, only two-dimensional images are selected and displayed as axi-symmetrical image NI, it is also possible that three-dimensional images are selected and displayed as composed three-dimensional hemifaces as axi-symmetrical image NI, for example in virtual reality applications and graphics renderings.

In the representations shown in FIGS. 3D to 3H, the symmetrical axis line SA is shown in the middle to illustrate the axi-symmetry of the image NI of the composite face having a face or face-like representation. However, preferably, with the goal that user U gets an uncompromised and clear view of the axi-symmetrical image NI of the composite face having a face or face-like representation, no such line or other graphical representation of symmetrical axis line SA is shown. Moreover, the button menu or control panel CP at the top right side of the window of graphical user interface GUI can also automatically disappear after a certain time, or can be located at a different location, or outside the window showing the image NI of the composite face having a face or face-like representation. Also for better merging of the two sides of image NI, a filter can be applied to the edge, for example but not limited to an edge softening filter, an edge-preserving smoothing, gradient transparency filter, this filter being applied with steps S50, S60, and S70.

With axi-symmetrical image NI of the composite face having a face or face-like representation as shown in FIGS. 3D to 3H, generated and modified by the steps S30, S50, S60, and S70, user U can take his time to appreciate, study, or immerse himself in analyzing the images, with the goal of evoking emotions, thereby axi-symmetrical image NI acting as an emotional stimulus. While the original image CS that was selected by step S20 may be a familiar face to user U, and already evoking certain emotions, the modified axi-symmetrical images NI can evoke different or amplified types of emotions, all by preserving a certain amount of familiarity with the originally selected subject represented by image CS.

By using these axi-symmetrical images NI with a composite face, a largely neglected and ignored aspect of facial stimuli for the study of reactions of a user U can be provided and used, for example a patient or other type of observer, is the fact that the two lateral sides of a face, for example a human or human-like face, convey principally different types of information to a viewer. In writings of Charles Darwin of 1872, it was suggested that the left hemiface of a posing animal or human person is more emotionally expressive than the right, an asymmetry later dubbed "facedness" by some authors. This is arguably due to the dominance of the right cerebral hemisphere, controlling the left half of the face, for emotional processing. See for example Borod et al., "Neuropsychological Aspects of Facial Asymmetry during Emotional Expression: A Review of the Normal Adult Literature," Neuropsychology Review Vol. 7, No. 1, year 1997, pp. 41-60, see also Thompson, J. Kevin, "Right brain, left brain; left face, right face: Hemisphericity and the expression of facial emotion," Cortex 21, No. 2, year 1985, pp. 281-299. In accordance with this assumption, generally speaking, the bias for the left hemiface can be more pronounced for negative emotions as it corresponds with the right hemisphere bias for negative affect, for example based on the "valence theories" of emotional hemispheric processing. See for example Tamagni et al., "Emotion and Space: Lateralized Emotional Word Detection depends on Line Bisection Bias," Neuroscience, Vol. 162, No. 4, year 2009, pp. 1101-1105. Facedness is also exaggerated in men compared to women, presumably as a consequence of a stronger hemispheric specialization of the male brain. It is also possible to measure a surface area of each hemiface LS, RS automatically to determine lateral dominance and asymmetries, according to the algorithm provided based on Koff et al., "Asymmetries for Hemiface Size and Mobility," Neuropsychologia Vol. 19, No. 6, 1981, pp. 825-830, or the algorithm of Nicholls et al., "Detecting Hemifacial Asymmetries in Emotional Expression with Three-Dimensional Computerized Image Analysis," Proceedings of the Royal Society of London. Series B: Biological Sciences, Vol. 271, No. 1540, year 2004, pp. 663-668. Thereby surface values of the area of each hemiface LS, RS can be used within the present method.

Figure 4:
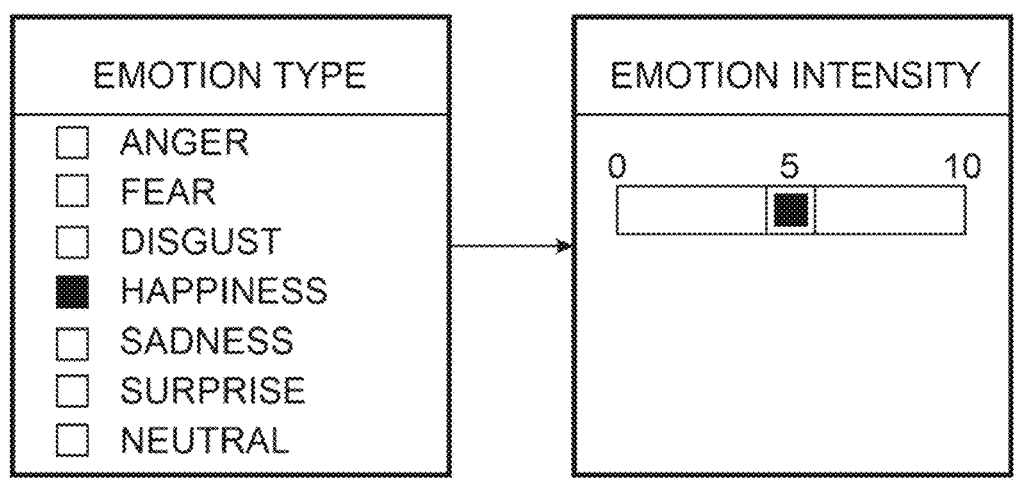
FIG. 4 shows an exemplary and simplified illustration of a user feedback questionnaire on the emotional mindset of user U that can be used for the step S80 where feedback can be provided by user U, that can be presented to the user U with a graphical user interface (GUI)

At any time after reviewing these axi-symmetrical images NI of the composite face having a face or face-like representation, user U can press, select, activate, or otherwise choose a button 43 of control panel CP to proceed to step S80 where feedback information can be provided by user U to computer system 100, for example by presenting a questionnaire to the user U, to request feedback on different feelings and their intensities, to evaluate his moods, feelings, emotions, or other aspects of his or her emotional state of mind, as illustrated in an exemplary embodiment of FIG. 4. For example, a graphical menu is displayed on a window of graphical user interface 40 can be displayed, where user U can select one or more seven (7) emotion types or mood types including, as a non-limiting example, anger, fear, disgust, happiness, sadness, surprise, and neutral feelings, and thereafter, the user U can enter an intensity of such a feeling, for example an intensity scale from 0 to 10. For example, it is possible that the face or face-like representation of FIGS. 3D to 3H is simultaneously displayed on the display screen while the feedback questions or information input menu or display is presented. With step S80, it is also possible that questions on feelings and emotional state of user U are asked by computer system 100 and played through speakers 12, and the user U can answer with oral responses, that are captured and analyzed by voice recognition. Instead of presenting direct questions on an emotional state of mind with the seven (7) emotion types, and the weighing thereof, different questions from an emotional mindset analysis questionnaire can be presented to user U, for example with screen windows in the GUI 40, or by audio played questions. The questions from the questionnaire, for the emotion regulation questionnaire (ERQ), emotion awareness questionnaire (EAQ), discrete emotions questionnaire (DEQ), Stimulus Evaluation Checks, (SEC), example see Crowley et al., "Evaluating a Brain-Computer Interface to Categorise Human Emotional Response," 10th IEEE International Conference on Advanced Learning Technologies, pp. 276-278, year 2010. In addition, step S80 can ask user U or therapist O about the thinking or personality type of the user U, so that the answers of user U can be normalized based on the thinking or personality type. For example, this can be based on the Myers-Briggs Type Indicator (MBTI) personality inventory, describing sixteen (16) personality types, ISTJ, ISFJ, INFJ, INTJ, ISTP, ISF, INFP, INTP, ESTP, ESFP, ENFP, ENTP, ESTJ, ESFJ, ENFJ, ENTJ, NEO-personality inventory (NEO PI) five factor model, or based on the four (4) functions of consciousness, including sensation, intuition, thinking, and feeling. It is possible that in step S80, a questionnaire is presented to the user U, for example by using the MBTI classification questionnaire, for using the MBTI classification scheme for the personality type of user U, or by using Keirsey Temperament Sorter (KTS) questionnaire, and thereafter using the KTS classification scheme.

With step S80 quantitative data of the subjective emotional state of mind of user U is made available to the computer system 100 by his or her data input, and this data can be used to analyze past events that the user U has been subject to, for example but not limited to past traumatic events, transformative events, joyful events, creativity events, for example by using the same computer system 100 using an automated analysis method. Also, with the data gathered by step S80, by having informed consent from user U who has observed images NI and has provided the emotional state feedback with step S80, it is also possible to provide for a contribution to provide analysis feedback to promote scientific advances in the neuropsychology of emotions. This concerns basic research in neurology and neuropsychiatry, but also applied research in clinical psychiatry and psychotherapy.

Next, a step S90 can be performed with method M100 to evaluate or analyze the responses received from step S80 of receiving feedback from user U, and for providing a results of the analysis with the computer system 100, as exemplarily visualized as a graphical user interface that can be displayed on screen 10 in FIG. 5. For example, this step can generate and provide a report with the classification of the human emotions of the user U, based on the moods, emotions, or feelings that user U experiences while viewing one or more of the observed images NI, and can displaying the report on the display screen 10, for example as a window of the graphical user interface 40. It is also possible that such report is sent to a third party, for example a remotely located therapist O, via network 50, for example with an email, message, file, for example via a cloud. For example, the report can include a thinking or personality type of user U, and an objective weighting of his emotions for which he has provided his or her input with step S80.

As of another example, this step S90 can provide information to a therapist of user U in the form of an objective emotional state of the user U, that is based on the weighting of the different types of emotions obtained from user input of step S80, that may have been subjective responses. For example, based on feedback received from user U with step S80, and information of his personality type, the different emotional factors can be corrected to generate a report on the objective moods, emotions, or feelings of the user U, based on the detected personality type, for example by comparing the responses or user input from step S80 with historic data of a mismatch between subjective responses and objective feelings of a group of people of the same personality type. For example, a similar approach using baseline data of likely feelings that would have been expressed by a person of the same personality trait, for as shown in U.S. Pat. No. 9,833,184, this reference herewith incorporated by reference in its entirety. See also International Patent Application No. PCT/GB2019/052846, this reference also herewith incorporated by reference in its entirety. In the variant shown in FIG. 5, the seven (7) different emotional states of mind are shown on a scale between one (1) to ten (10), after the normalization, to show an objective state of mind of user U. Also, the identified personality type is displayed, in the example shown a MBTI classification as Extraverted, Sensing, Feeling, Perceiving (ESFP). As of another aspect, step S90 can also provide for a summary of the emotional state reported by user U in step S80.

According to another aspect, it is also possible that steps S80 of feedback input and step S90 of evaluating or analyzing are performed with detection and measurement of different physiological values of user U, physiognomical values of user U, or a combination of both. In this respect, instead of receiving manually-input data from user U with a input device 22, 26, of computer system 100, it is also possible that the face of user U is analyzed automatically for detection the different types of moods, emotions, or feelings by computer algorithms, for example with a an image capturing device 28 that is operatively connected to an image-based analysis system with a data processor, for example a data processor and algorithms of computer system 100, where image sequences are captured from his or her face during the observation of the image NI, to determine different types of emotions from his or her facial expressions with computer algorithms, see for example U.S. Pat. No. 11,048,921 with an artificial intelligence approach, and U.S. Pat. No. 8,235,725 and U.S. Patent Publication No. 2015/0305662, based on facial features tracking. Also, in a variant, it is possible that different types of physiological values are measured from user U and are interpreted to detect different types of moods, emotions, or feelings, as shown in U.S. Pat. No. 9,833,184, based on different measured physiological responses, such as breathing patterns, cardiac response, posture, etc. or are based on thermal images that are captured from the face of user U, see for example Cruz-Albarran et al., "Human Emotions Detection Based on a Smart-Thermal System of Thermographic Images," Infrared Physics & Technology, Vol. 81, year 2017, pp. 250-261, Salazar-Lopez et al., "The Mental and Subjective Skin: Emotion, Empathy, Feelings and Thermography," Consciousness and cognition, Vol. 34 year 2015, pp. 149-162, Chotard et al., "Infrared Thermal Imaging: Positive and Negative Emotions Modify the Skin Temperatures of Monkey and Ape Faces," American Journal of Primatology, Vol. 80, No. 5, year 2018, e22863, Nummenmaa et al., "Bodily Maps of Emotions," Proceedings of the National Academy of Sciences, Vol. 111, No. 2, year 2014, pages 646-651, these references herewith incorporated by reference in their entirety.

The herein presented method M100 and system 100 also takes advantage of the human mind of a patient or other human being under analysis that can perceive a specific, often meaningful image, for example a face, in a random or ambiguous visual patterns, for example solely based on three points, this effect being known to called the Pareidolia. This allows the human being to recall positive or negative memories that may have been recorded in conjunction with the face or face-like features detected from the visual pattern.

According to some aspects of the present invention, with method M100 and system 100, a therapist O, for example a psychotherapist or other psychology or psychiatry professional has access to a computerized tool to treat, analyze, or examine a patient as user U, the analysis based on the thesis that human beings, such as user U, tend to subconsciously record a latently remaining emotional pain or memories of past traumatic events and emotional injuries into their soul. This latently or coveted remaining emotional pain can be experienced and felt by user U if a certain emotional pressure or stimulus is applied to user U in the context of the past experience, even many years after the traumatic event or emotional injury has occurred. Similarly as physical injures to which a user U may have been subject to, these physical injuries can also be felt for many years on the body and during bodily motions of user U. Also, such latently remaining emotional pain or memories of a past traumatic event, or at least a large portion thereof, is often stored or memorized together in conjunction with a memories of a person, for example a person that was an important attachment figure or reference person for user U. By the visualization of a face or a face-like representation of such reference person, for example a person from a circle of friends of user U at time of occurrence of the past traumatic event, it is possible to use a selected image CS, and a modification as an axi-symmetric image NI to open a discussion of the emotional state of user U, for example with therapist O as an operator or by a computer analysis with step S90, for reprocessing and ultimately healing purposes. Unprocessed or unhealed latent and subconscious emotional pain can hinder and prevent full use of our positive energy for life and for specific life situations, and thereby also cause a certain emotional vulnerability for a user U, and a reduction of an emotional resistance to specific stressful or traumatic events. For example, method M100 can be employed by emotionally stable individuals who would like to use their full emotional potential, or by individuals who would like to overcome a dispute or conflict in a human relationship. Also, method M100 can also be used for professionals in the psychology or psychiatry profession, as a supporting tool that can provide for some guidance in the psychoanalysis of a potential patient or for self-psychoanalysis. It may also be possible that method M100 can be used as a psychotherapy tool for treating individuals with strong psychological problems and instabilities, or individuals with psychosomatic symptoms and ailments, by using concept of psychoanalysis originally formulated by Sigmund Freud and Heinz Kohut.

In addition, the image FI of the face or a face-like representation used in the context of method M100 to generate axi-symmetric image NI to can also be a representation of a figure or face of a having spiritual, religious or historic meaning to certain people, nation, tribe, religious community, cult, for example a depiction of buddha, as an example but not limited to a depiction of Kamakura Daibutsu as the great buddha of Japan, depiction of Jesus, depiction of the pope, depiction of ecumenical patriarch of Constantinople, depiction of hindu gods and goddesses such as but not limited to Brahma, Vishnu, Shiva, Ganapati, Durga Devi, depiction of historic leaders and abstractions of these depictions, including cartoonizations, pixelations, paintings thereof.

Because method M100 and system 100 is based on the selection of a picture template or stimulus SC selected by the patient or user U, it is possible to substantially shorten a psychoanalysis procedure, which usually requires awkward and verbally lengthy discussions and proceedings that can be avoided, for example based on methods from Sigmund Freud and Heinz Kohut. See for example Kohut, Heinz, "The Analysis of the Self: A Systematic Approach to the Psychoanalytic Treatment of Narcissistic Personality Disorders," University of Chicago Press, 2013. The therapist O can enter into dialogue with the patient or user U directly via the metaphor presented by the selected image CS and the axy-symmetrical representations NI thereof, for example with the use of computer or display screen 100 and the GUI.

The therapist O is verbally trained and can understand the personality of the patient, for example by asking structured questions, for example questions from the above-mentioned questionnaires, the ones of step S80, or similar ones. These can also be automatically presented to patient or user U with step S80. The patient or user U is untrained in this and it can therefore be helpful to additionally approach his or her emotional pain issues and old subconsciously present emotional wounds with the help of the selected image CS and the axi-symmetric images NI. In addition, the patient or user U has often trained himself or herself to create a psychological barrier of avoidance behavior, which can be circumvented with an approach via figurative language.

When using method M100, if possible, the therapist O should not exert any influence in the choice of the selected image CS for the emotional metaphor of step S20, and it should be done independently by user U. At the beginning of the therapy, it can be useful to first do some exercises with the patient using portraits of famous people. In addition, the therapist can, depending on his or her abilities, enhance the effect of the image metaphor described by the patient with graphic tools, for example by using steps S30, S40, S50, S60, and S70 of method M100. Together with the patient or user U, the therapist O can develops a plan for the sequence of analysis of the reference persons that can become represented by a selected image SI, for example by presenting a series of reference images FI1 to FI4 as shown in FIG. 3A. It is also possible that method M100 includes an additional step of capturing and uploading a self-portrait to images FI1 to FI4, for example a plurality of different self-portraits, and thereby therapist or operator O can use the self-portrait for the emotional assessment of user or patient U.

Generally speaking, according to an aspect of method M100, it is possible to progress with less time spent in sessions using the steps of method M100, as compared to a full and exclusive verbal personality analysis. However, some time may be needed between different sessions with method M100 so that the image metaphor with selected image CS developed can unfold its effect in the consciousness of user or patient U. It may take up to four (4) weeks for the full effect to unfold, when analyzing an individual with method M100. The success can be shown by a noticeable emotional relief when thinking about this reference person of selected image CS. In the meantime, it is also possible to work on another reference person with a selected image CS, in a parallel or subsequent session of method M100. The effect of the developed image metaphor of selected image CS, for example by the image modifications of steps S60 and S70 is stronger and can have an amplified effect for the consciousness as compared to the effect of the already existing and unprocessed images FI1 to FI4 to this reference person. This can be explained by the fact that with the new image metaphor that is provided by the modifications by steps S60 and S70, and the person represented in the selected image CS, often the essence of the relationship to user or patient U can come to light quicker. To put this effect into words seems hardly possible.

Another aspect of the present invention is the including of method M100 into a computer simulation, virtual reality, or gaming environment. For example, in different types of virtual reality or gaming settings, it may be useful to elicit specific emotions to a user U. This can be done by using images of known personalities to elicit emotions, for example but not limited to using images of polarizing politicians, celebrities, nemesis, virtual and real personalities. For example, an avatar or other virtual representation of a human-like gaming character can be used as a basis for the selected image CS, to generate an axy-symmetrical representations NI thereof. For example, in the exemplary context of the video game Minecraft or other virtual-reality type gaming or exploration environments, it is possible to present axi-symmetric images NI to users U, also as three-dimensional variants thereto. As of another aspect of the present invention, the method M100 can be part of a computer-assisted psychology assessment tool or environment, or a mental health analysis software, or a remote or online psychology tool for assessing different patients remotely, where method M100 can be performed as a tool, activity, course, or training session, within the context of a larger psychological analysis of a user U, see for example the software Quenza™ coaching software for psychologists, mental health practitioners, therapists.

Other applications of the herein described method M100 are the integration or availability of the tool human resources (HR) purposes for assessing suitability and performance of a specific candidate or user, as an example in the context of an automated HR software tool such as HireVue™ or Vervoe™. By using method M100 and by asking specific questions to a user or candidate for a job or position, in relation to the displayed axi-symmetrical images, it is possible to obtain a more detailed psychological analysis of the user or candidate, without the need of passing lengthy psychoanalysis sessions or in-person meetings.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:

1. A computer system for performing psychoanalysis on a human being, the system including a computing device including a display screen operating a graphical user interface and a data processor, the data processor configured to:
   access an image, the image representing human, animal, human-like, or animal-like facial features;
   generate a mirrored image from the provided image about a vertical mirror axis with a data processor of the computing device;
   partially superpose the provided image and the mirrored image to create a vertical axi-symmetric image, one side of the vertical mirror axis showing a portion of the provided image, the other side showing a portion of the mirrored image; and
   display the vertical axi-symmetric image on the graphical user interface of the computing device.

2. The system of claim 1, wherein the data processor is further configured to:
   present a plurality of questions to the human being requesting information on an emotional state of mind of the human being; and
   analyze the information by the computing device to classify the emotional state of mind of the human being based on a human emotions model.

3. The system of claim 2, wherein the data processor is further configured to:
   provide a report with the classification of the human emotions of the living being, and display the report on the display screen.

4. The system of claim 2, wherein the plurality of questions include questions from at least one of an emotion regulation questionnaire (ERQ), discrete emotions questionnaire (DEQ), emotional stability questionnaire, emotion awareness questionnaire (EAQ).

5. The system of claim 1, wherein the data processor is further configured to:
   present a plurality of pre-stored images to the human being on the graphical user interface of the display screen, each one of the plurality of images representing human, animal, human-like, or animal-like facial features; and
   permit a selection of one of the plurality images with an input device as the provided image by the human being, the selected image being such that it causes a positive or a negative emotion to the human being based on the facial features.

6. A computerized method for performing psychoanalysis on a human being, the method performed on a computing device having a display screen operating a graphical user interface, the method comprising the steps of:
   providing an image to the computing device, the image representing human, animal, human-like, or animal-like facial features;
   generating a mirrored image from the provided image about a vertical mirror axis with a data processor of the computing device;
   partially superposing the provided image and the mirrored image to create a vertical axi-symmetric image, one side of the vertical mirror axis showing a portion of the provided image, the other side showing a portion of the mirrored image; and
   displaying the vertical axi-symmetric image on the graphical user interface of the computing device.

7. The computerized method of claim 6, further comprising the steps of
   presenting a plurality of pre-stored images to the human being on the graphical user interface of the display screen, each one of the plurality of images representing human, animal, human-like, or animal-like facial features; and
   permitting a selection of one of the plurality images with an input device as the provided image by the human being, the selected image being such that it causes a positive or a negative emotion to the human being based on the facial features.

8. The computerized method of claim 6, further comprising the step of:
   moving the provided image relative to the mirrored image along a horizontal axis to change an appearance of the vertical axi-symmetric image on the graphical user interface, after the step of partially superposing, by an operation via the input device.

9. The computerized method of claim 6, further comprising the step of:
   presenting a plurality of questions to the human being requesting information on an emotional state of mind of the human being; and
   analyzing the information by the computing device to classify the emotional state of mind of the human being based on a human emotions model.

10. The computerized method of claim 9, wherein the human emotions model include emotional factors including anger, fear, disgust, happiness, sadness, surprise, and neutral feelings.

11. The computerized method of claim 9, further comprising a step of:
   providing a report with the classification of the human emotions of the living being, and displaying the report on the display screen.

12. The computerized method of claim 9, wherein the plurality of questions include questions from at least one of an emotion regulation questionnaire (ERQ), discrete emotions questionnaire (DEQ), emotional stability questionnaire, emotion awareness questionnaire (EAQ).

13. The computerized method of claim 9, wherein in the step of analyzing the information to classify the emotional state of mind, the classification of the human emotions of the human being are normalized based on a thinking or personality type of the human being.

14. The computerized method of claim 6, wherein the step of providing includes a scanning of a photograph selected by the human being, or an uploading of a digital image chosen by the human being from an external device.

15. A non-transitory computer readable medium having computer instructions recorded thereon, the computer instructions configured to perform a method when executed on a computer system having a display device, the method configured to perform psychoanalysis on a human being, the method including the steps of:
   providing an image to the computing device, the image representing human, animal, human-like, or animal-like facial features;
   generating a mirrored image from the provided image about a vertical mirror axis with a data processor of the computing device;
   partially superposing the provided image and the mirrored image to create a vertical axi-symmetric image, one side of the vertical mirror axis showing a portion of the provided image, the other side showing a portion of the mirrored image; and
   displaying the vertical axi-symmetric image on the graphical user interface of the computing device.

16. The non-transitory computer readable medium of claim 15, wherein the method further comprises:
   presenting a plurality of questions to the human being requesting information on an emotional state of mind of the human being; and
   analyzing the information by the computing device to classify the emotional state of mind of the human being based on a human emotions model.

17. The non-transitory computer readable medium of claim 15, wherein the method further comprises:
   presenting a plurality of pre-stored images to the human being on the graphical user interface of the display screen, each one of the plurality of images representing human, animal, human-like, or animal-like facial features; and
   permitting a selection of one of the plurality images with an input device as the provided image by the human being, the selected image being such that it causes a positive or a negative emotion to the human being based on the facial features.

18. The non-transitory computer readable medium of claim 16, wherein the method further comprises:
   presenting a plurality of questions to the human being requesting information on an emotional state of mind of the human being; and
   analyzing the information by the computing device to classify the emotional state of mind of the human being based on a human emotions model.

19. The non-transitory computer readable medium of claim 18, wherein the human emotions model include emotional factors including anger, fear, disgust, happiness, sadness, surprise, and neutral feelings.

* * * * *